(12) United States Patent
Silvestrini et al.

(10) Patent No.: US 10,016,301 B2
(45) Date of Patent: Jul. 10, 2018

(54) OCULAR IMPLANT WITH SHAPE CHANGE CAPABILITIES

(71) Applicant: Novartis AG, Basel (CH)

(72) Inventors: Thomas A. Silvestrini, Alamo, CA (US); Steven John, Menlo Park, CA (US); Jose Garcia, Fremont, CA (US); Richard S. Lilly, Menlo Park, CA (US)

(73) Assignee: Novartis AG, Basel (CH)

( * ) Notice: Subject to any disclaimer, the term of this patent is extended or adjusted under 35 U.S.C. 154(b) by 69 days.

(21) Appl. No.: 14/140,322

(22) Filed: Dec. 24, 2013

(65) Prior Publication Data

US 2014/0107556 A1    Apr. 17, 2014

Related U.S. Application Data

(63) Continuation of application No. 12/492,051, filed on Jun. 25, 2009, now Pat. No. 8,617,139.
(Continued)

(51) Int. Cl.
| | |
|---|---|
| *A61M 37/00* | (2006.01) |
| *A61F 9/007* | (2006.01) |
| *A61M 5/00* | (2006.01) |
| *A61M 1/00* | (2006.01) |
| *A61M 31/00* | (2006.01) |
| *A61M 25/00* | (2006.01) |

(52) U.S. Cl.
CPC ......... *A61F 9/00781* (2013.01); *A61M 37/00* (2013.01)

(58) Field of Classification Search
CPC .......... A61M 37/00; A61M 5/00; A61M 1/00; A61M 31/00; A61M 25/00; A61M 35/00; A61N 1/30; A61K 9/02; A61B 5/117; A61B 3/16; A61L 33/00; B05D 3/00
USPC ............................................... 604/5.04, 8–10
See application file for complete search history.

(56) References Cited

U.S. PATENT DOCUMENTS

| | | | |
|---|---|---|---|
| 3,767,759 A | 10/1973 | Wichterle | |
| 3,788,327 A | 1/1974 | Donowitz et al. | |

(Continued)

FOREIGN PATENT DOCUMENTS

| | | | |
|---|---|---|---|
| CA | 2718294 A1 * | 4/2001 | |
| EP | 0 228 185 A1 | 11/1986 | |

(Continued)

OTHER PUBLICATIONS

U.S. Appl. No. 11/615,810, filed Dec. 22, 2006, 2007-0191863.
(Continued)

*Primary Examiner* — Tatyana Zalukaeva
*Assistant Examiner* — Ilya Treyger
(74) *Attorney, Agent, or Firm* — Mintz Levin Cohn Ferris Glovsky and Popeo, P.C.

(57) ABSTRACT

Disclosed are devices, methods and systems for treatment of eye disease such as glaucoma. Implants are described herein that enhance aqueous flow through the normal outflow system of the eye with minimal to no complications. The implant can be reversibly deformed to a first shape, such as a generally linear shape conducive to insertion. Upon insertion, the implant can deform to a second shape, such as a generally non-linear shape conducive to retention within the eye. The shape also improves fluid flow from the anterior chamber and prevents or reduces clogging.

7 Claims, 10 Drawing Sheets

Related U.S. Application Data

(60) Provisional application No. 61/076,121, filed on Jun. 26, 2008, provisional application No. 61/075,706, filed on Jun. 25, 2008.

(56) References Cited

U.S. PATENT DOCUMENTS

| | | |
|---|---|---|
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,634,418 A | 1/1987 | Binder |
| 4,722,724 A | 2/1988 | Schocket |
| 4,750,901 A | 6/1988 | Molteno |
| 4,787,885 A | 11/1988 | Binder |
| 4,826,478 A | 5/1989 | Schocket |
| 4,846,172 A | 7/1989 | Berlin |
| 4,886,488 A | 12/1989 | White |
| 4,900,300 A | 2/1990 | Lee |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,397,300 A | 3/1995 | Baerveldt et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,556,427 A * | 9/1996 | Durette ................. 623/6.64 |
| 5,558,629 A | 9/1996 | Baerveldt et al. |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,752,928 A | 5/1998 | de Roulhac et al. |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,899,935 A * | 5/1999 | Ding ................. A61F 2/90 |
| | | 623/1.53 |
| 5,968,058 A | 10/1999 | Richter et al. |
| 6,007,510 A | 12/1999 | Nigam |
| 6,007,511 A | 12/1999 | Prywes |
| 6,019,786 A * | 2/2000 | Thompson ................. 623/1.13 |
| 6,050,970 A | 4/2000 | Baerveldt |
| 6,077,299 A | 6/2000 | Adelberg et al. |
| 6,102,045 A | 8/2000 | Nordquist et al. |
| 6,142,969 A | 11/2000 | Nigam |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,331,313 B1 | 12/2001 | Wong et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | de Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | de Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,709 B2 * | 10/2008 | Pinchuk et al. ................. 604/8 |
| 7,431,710 B2 * | 10/2008 | Tu et al. ................. 604/8 |
| 7,488,303 B1 | 2/2009 | Haffner et al. |
| 7,857,782 B2 | 12/2010 | Tu et al. |
| 8,034,105 B2 | 10/2011 | Stegmann et al. |
| 2002/0013546 A1 | 1/2002 | Grieshaber et al. |
| 2002/0072673 A1 | 6/2002 | Yamamoto et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0177856 A1 | 11/2002 | Richter et al. |
| 2002/0193725 A1 | 12/2002 | Odrich |
| 2003/0060752 A1 | 3/2003 | Bergheim et al. |
| 2003/0097151 A1 | 5/2003 | Smedley et al. |
| 2003/0097171 A1 | 5/2003 | Elliott |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |

(56) References Cited

U.S. PATENT DOCUMENTS

| | | |
|---|---|---|
| 2004/0088048 A1 | 5/2004 | Richter et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0049578 A1 | 3/2005 | Tu et al. |
| 2005/0085892 A1* | 4/2005 | Goto et al. .................. 623/1.12 |
| 2005/0090806 A1 | 4/2005 | Lynch et al. |
| 2005/0090807 A1 | 4/2005 | Lynch et al. |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0250788 A1 | 11/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0288617 A1 | 12/2005 | Yaron et al. |
| 2005/0288619 A1 | 12/2005 | Gharib et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241749 A1 | 10/2006 | Tu et al. |
| 2007/0010827 A1 | 1/2007 | Tu et al. |
| 2007/0088242 A1 | 4/2007 | Coroneo |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0149915 A1 | 6/2007 | Yablonski |
| 2007/0191863 A1* | 8/2007 | De Juan et al. .............. 606/108 |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0182421 A1 | 7/2009 | Silvestrini et al. |
| 2010/0010416 A1 | 1/2010 | Juan, Jr. et al. |

FOREIGN PATENT DOCUMENTS

| | | |
|---|---|---|
| EP | 1173124 A1 | 1/2002 |
| EP | 1173125 A1 | 1/2002 |
| EP | 1173126 A1 | 1/2002 |
| EP | 1184010 A2 | 3/2002 |
| EP | 1310222 A2 | 5/2003 |
| EP | 1473004 A2 | 11/2004 |
| EP | 1477146 A2 | 11/2004 |
| EP | 1418868 B1 | 3/2008 |
| EP | 1977724 A1 | 10/2008 |
| EP | 1545655 B1 | 12/2008 |
| EP | 2027837 A2 | 2/2009 |
| GB | 2101891 A | 1/1983 |
| WO | WO-89/00869 A1 | 2/1989 |
| WO | WO-91/12046 A1 | 8/1991 |
| WO | WO-92/19294 A1 | 11/1992 |
| WO | WO-94/09721 A1 | 5/1994 |
| WO | WO-94/09837 A1 | 5/1994 |
| WO | WO-94/13234 A1 | 6/1994 |
| WO | WO-96/20742 A1 | 7/1996 |
| WO | WO-96/36377 A1 | 11/1996 |
| WO | WO-98/23237 A1 | 6/1998 |
| WO | WO-98/30181 A1 | 7/1998 |
| WO | WO-99/26567 A1 | 6/1999 |
| WO | WO-00/06223 A1 | 2/2000 |
| WO | WO-00/64389 A1 | 11/2000 |
| WO | WO-00/64511 A1 | 11/2000 |
| WO | WO-01/078631 A2 | 10/2001 |
| WO | WO-01/78656 A2 | 10/2001 |
| WO | WO-01/097727 A1 | 12/2001 |
| WO | WO 02/036052 | 5/2002 |
| WO | WO-02/070045 A1 | 9/2002 |
| WO | WO-02/074052 A2 | 9/2002 |
| WO | WO-02/080829 A2 | 10/2002 |
| WO | WO-02/087418 A2 | 11/2002 |
| WO | WO-02/087479 A2 | 11/2002 |
| WO | WO-02/089699 A2 | 11/2002 |
| WO | WO-02/102274 A2 | 12/2002 |
| WO | WO-03/015659 A2 | 2/2003 |
| WO | WO-03/015667 A1 | 2/2003 |
| WO | WO-03/073968 A2 | 9/2003 |
| WO | WO-03/099175 A1 | 12/2003 |
| WO | WO-2004/026347 A2 | 4/2004 |
| WO | WO-2004/043231 A2 | 5/2004 |
| WO | WO-2004/056294 A1 | 7/2004 |
| WO | WO-2004/060219 A1 | 7/2004 |
| WO | WO-2004/062469 A2 | 7/2004 |
| WO | WO-2004/110391 A2 | 12/2004 |
| WO | WO-2005/016418 A1 | 2/2005 |
| WO | WO-2005/046782 A1 | 5/2005 |
| WO | WO-2005/055873 A2 | 6/2005 |
| WO | WO-2005/105197 A2 | 11/2005 |
| WO | WO-2005/107664 A2 | 11/2005 |
| WO | WO-2005/107845 A1 | 11/2005 |
| WO | WO-2006/012421 A2 | 2/2006 |
| WO | WO-2006/036715 A2 | 4/2006 |
| WO | WO-2007/087061 A2 | 8/2007 |
| WO | WO-2007/115259 A2 | 10/2007 |
| WO | WO-2007/130393 A2 | 11/2007 |
| WO | WO-2008/061043 | 5/2008 |
| WO | WO-2009/158524 A2 | 12/2009 |

OTHER PUBLICATIONS

U.S. Appl. No. 11/624,168, filed Jan. 17, 2007, 2007-0233037.
U.S. Appl. No. 12/175,294, filed Jul. 17, 2008, 2009-0182421.
U.S. Appl. No. 12/561,680, filed Sep. 17, 2009, 2010-0010416.

(56) References Cited

OTHER PUBLICATIONS

U.S. Appl. No. 12/898,593, filed Oct. 5, 2010, 2011-0028883.
U.S. Appl. No. 12/905,003, filed Oct. 14, 2010, 2011-0028884.
U.S. Appl. No. 12/939,033, filed Nov. 3, 2010, 2011-0105990.
U.S. Appl. No. 12/970,482, filed Dec. 16, 2010, 2011-0098629.
U.S. Appl. No. 12/972,176, filed Dec. 17, 2010, 2011-0087149.
U.S. Appl. No. 12/972,261, filed Dec. 17, 2010, 2011-0087150.
U.S. Appl. No. 12/972,325, filed Dec. 17, 2010, 2011-0087151.
U.S. Appl. No. 13/365,175, filed Feb. 2, 2012, 2012-0220917.
U.S. Appl. No. 13/656,326, filed Oct. 19, 2012, 2013-0103145.
U.S. Appl. No. 13/865,927, filed Apr. 18, 2013, 2013-0281817.
U.S. Appl. No. 13/865,947, filed Apr. 18, 2013, 2013-0281908.
U.S. Appl. No. 13/897,313, filed May 17, 2013, 2013-0253407.
U.S. Appl. No. 14/025,145, filed Sep. 12, 2013, 2014-0012279.
U.S. Appl. No. 14/042,546, filed Sep. 30, 2013, 2014-0031737.
PCT/US2012/061141, Oct. 19, 2012, WO 2013/059678.
PCT/US2013/037234, Apr. 18, 2013, WO 2013/158919.
Bick M.W., "Use of tantalum for ocular drainage" Arch Ophthal. Oct. 1949; 42(4): 373-88.
Bietti, G., "The present state of the use of plastics in eye surgery" Acta Ophthalmol (Copenh) 1955; 33(4):337-70.
Classen et al., "A histopathologic and immunohistorchemical analysis of the filtration bleb after unsuccessful glaucoma seton implantation" Am. J. Ophthalmol. 122:205-12 (1996).
Cohen et al., "First day post-operative review following uncomplicated phacoemulsification" Eye 12(4):634-6 (1998).
Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].
Dinakaran et al., "Is the first post-operative day review necessary following uncomplicated phacoemulsification surgery?" Eye, 14(3A):364-6 (2000).
Einmahl et al., "Evaluation of a novel biomaterial in the suprachoroidal space of the rabbit eye" Invest Ophthalmol Vis Sci. 43:1533-1539 (2002).
Emi et al., "Hydrostatic pressure of the suprachoroidal space" Invest. Ophthal. Visual Sci. 30(2):233-238 (1989).
Fuchs E., "Detachment of the choroid inadvertently during cataract surgery" [German] von Graefes Arch Ophthalmol, 51:199-224 (1900) [Article in German with English summary].
Gills et al., "Action of cyclodialysis utilizing an implant studied by manometry in a human eye" Expl Eye Res 1967; 6:75-78.
Gills JP, "Cyclodialysis implants" South Med J. 1967 60(7):692-5.
Gross et al., "Surgical therapy of chronic glaucoma in aphakia and pseudophakia" Ophthalmology, 95:1195-201 (1988).
Heine I., "Cyclodialysis, a new glaucoma operation" Dtsch Med Wochenschr, 31:824-826 (1905) [Article in German with English summary included].
Hildebrand et al., "Efficacy of anterior chamber decompression in controlling early intraocular pressure spikes after uneventful phacoemulsification" J. Catact Refract Surg., 29:1087-92 (2003).

Howorth DJ, "Feasibility study for a micromachined glaucoma drainage device" Cranfield University School of industrial and manufacturing science MSc Thesis Academic Year 2001-2002 Sep. 13, 2002.
Hylton et al., "Update on prostaglandin analogs" Curr Opin Ophthalmol, 14:65-9 (2003).
Jordan J., "A Novel Approach to Suprachoroidal Drainage for the Surgical Treatment of Intractable Glaucoma" J. Glaucoma 2006; 15:200-205.
Karlen, M. et al., "Deep sclerectomy with collagen implant: medium term results" Br. J. Ophthalmol, Jan. 1999, 83(1):6-11.
Klemm et al., "Experimental use of space-retaining substances with extended duration: functional and morphological results" Graefes Arch Clin Exp Ophthalmol Sep. 1995; 233(9):592-7.
Kozlov et al., "Nonpenetrating deep sclerectomy with collagen" Eye microsurgery 3:44-46 (1990) [Article in Russian with English translation included].
Krejci, L., "Cyclodialysis with hydroxymethyl methacrylate capillary strip (HCS). Animal experiments with a new approach in glaucoma drainage surgery" Ophthalmologica 1972; 164(2):113-21.
Lee et al., "Magnetic resonance imaging of the aqueous flow in eyes implanted with the trabeculo-suprachoroidal glaucoma seton" Invest. Ophthalmol. Vis. Sci. 33:948 (1992).
Losche, W., "Proposals for improvement of cyclodialysis" Klin Monatsblatter Augenheilkd Augenarztl Fortbild 1952 121(6):715-6 [Article in German with English translation included].
Nesterov, AP, et al., "Surgical stimulation of the uveoscleral outflow. Experimental studies on enucleated human eyes" Acta Opthalmol (Copenh) June; 57(3):409-17 (1979).
Ozdamar, A., et al., "Suprachoroidal seton implantation in refractory glaucoma: a novel surgical technique" J. Glaucoma Aug. 2003; 12(4):354-9.
Pinnas, G. et al. "Cyclodialysis with teflon tube implants" Am J. Ophthalmol 1969 Nove; 68(5):879-883.
Rosenberg, L., et al. "Implants in glaucoma surgery" Chapter 88, The Glaucomas, Ritch et al. Eds. 2nd Ed. Mosby St. Louis 1986; p. 1783-1807.
Row, H., "Operation to control glaucoma: preliminary report"(1934) Arch. Ophthal 12:325.
SOLX Clinical Literature Handout; Industry Show Feb. 2006; "The SOLX Gold Micro-shunt (GMS) treatment".
Srinivasan, R., et al., "Microbial contamination of the anterior chamber during phacoemulsification" J. Cataract Refract Surg. 28:2173-6 (2002).
Toris, C., et al., "Aqueous humor dynamics in the aging human eye" Am J. Ophthalmol., 127:407-12 (1999).
Troncosco, U.M., "Cyclodialysis with insertion of metal implant in treatment of glaucoma Preliminary report" Arch. Ophthal. 23:270 (1940).
Yablonski, "Trabeculectomy with Internal Tube Shunt: a novel glaucoma surgery" J. Glaucoma 14:91-97 (2005).
Yablonski, M., "Some thoughts on the pressure dependence of uveoscleral flow" Journal of Glaucoma, 12(1):90-92 (2003).
Zhou, J., et al., "A trabecular bypass flow hypothesis" J Glaucoma. 14(1):74-83 (2005).

\* cited by examiner

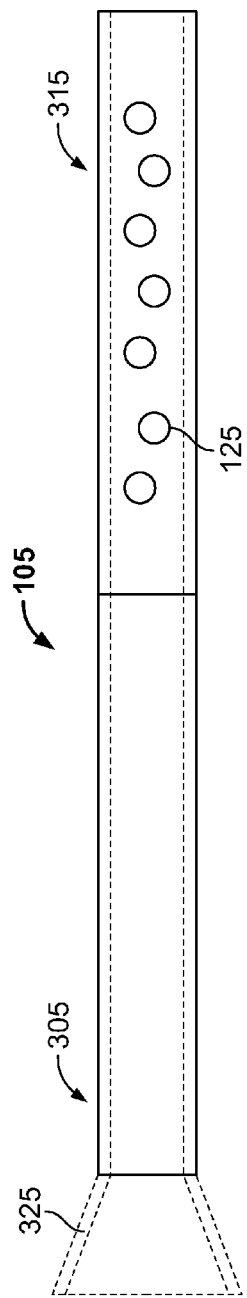
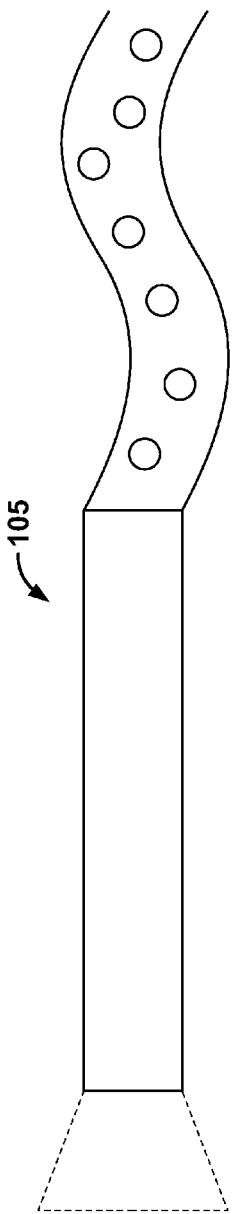

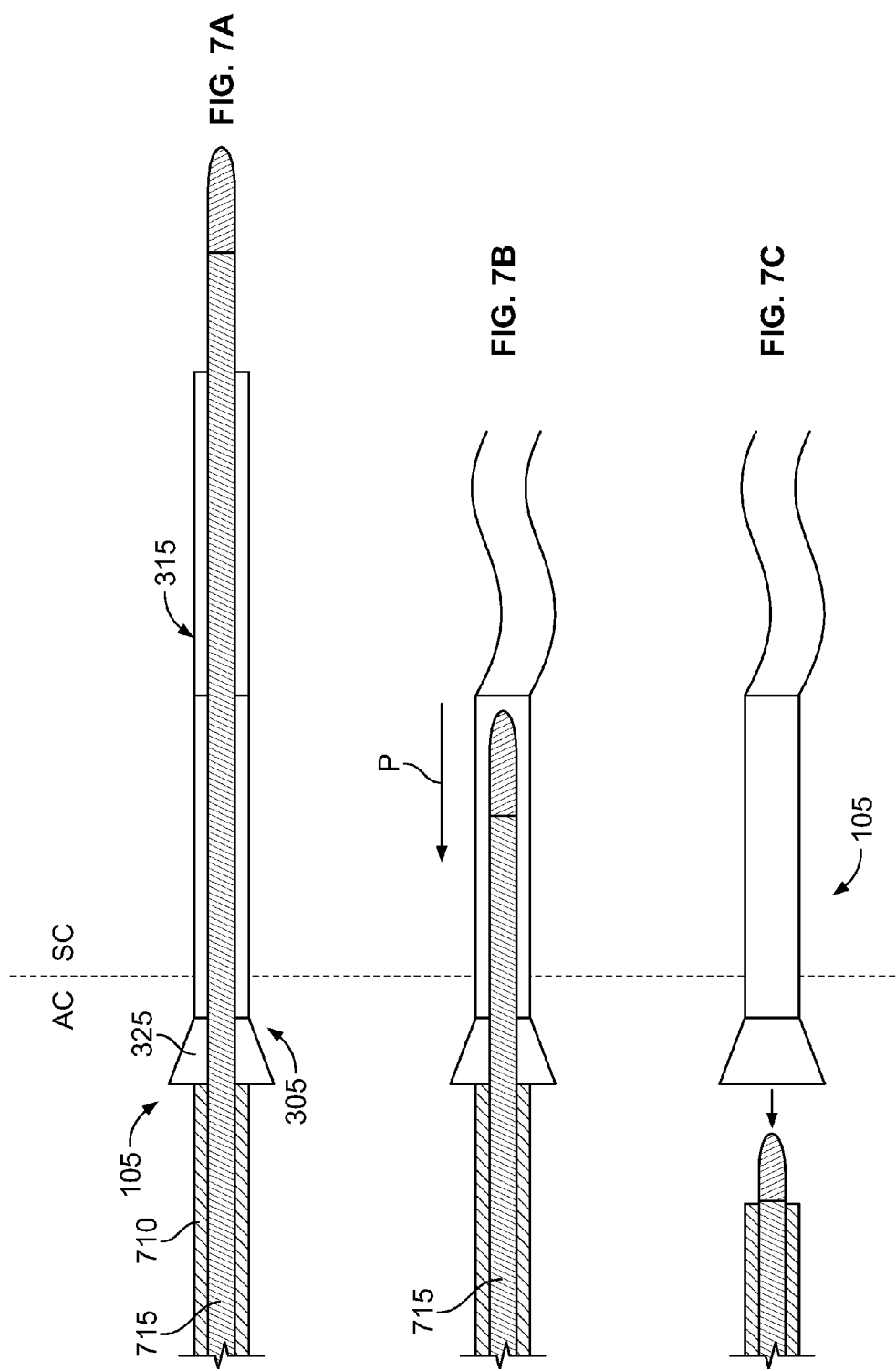

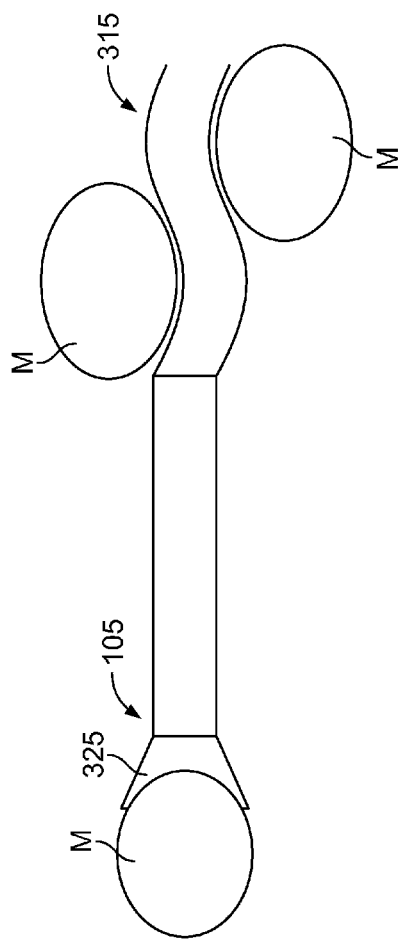
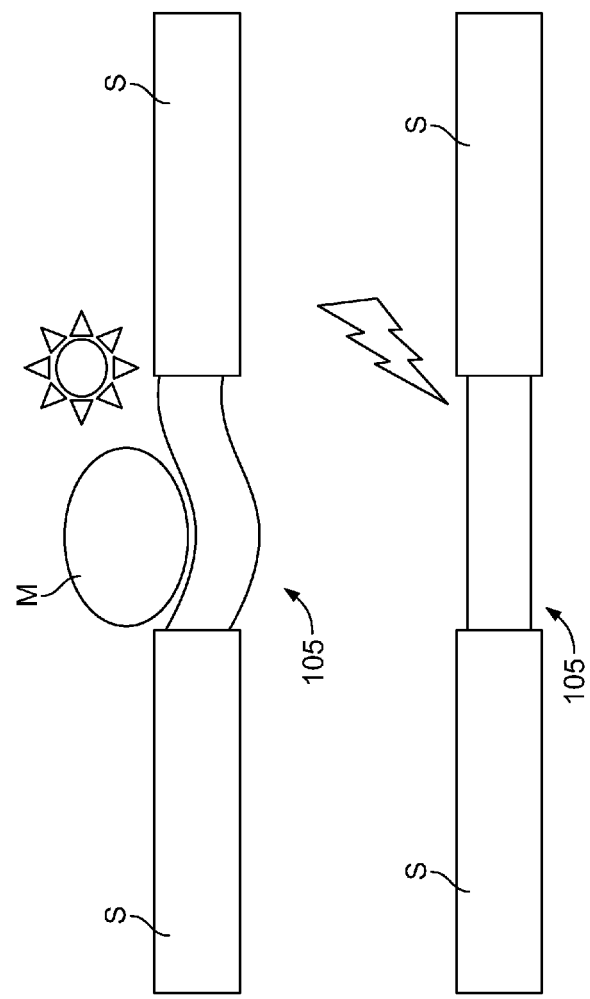

OCULAR IMPLANT WITH SHAPE CHANGE CAPABILITIES

CROSS REFERENCE TO RELATED APPLICATIONS

This application is a continuation of U.S. patent application Ser. No. 12/492,051, entitled "Ocular Implant with Shape Change Capabilities," filed Jun. 25, 2009, which in turn claims priority of U.S. Provisional Patent Application Ser. Nos. 61/075,706, entitled "Ocular Implant Having Braided Structure" by Thomas Silvestrini, filed Jun. 25, 2008, and 61/076,121, entitled "Ocular Implant with Shape Change Capabilities" by Thomas Silvestrini, filed Jun. 26, 2008. Priority of the filing dates of Jun. 25, 2008 and Jun. 26, 2008 is hereby claimed, and the disclosures of the aforementioned Patent Applications are hereby incorporated by reference.

BACKGROUND

This disclosure relates generally to methods and devices for use in treating glaucoma. The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Past treatment includes the use of drugs that lower intraocular pressure through various mechanisms. The glaucoma drug market is an approximate two billion dollar market. The large market is mostly due to the fact that there are not any effective surgical alternatives that are long lasting and complication-free. Unfortunately, drug treatments need much improvement, as they can cause adverse side effects and often fail to adequately control intraocular pressure. Moreover, patients are often lackadaisical in following proper drug treatment regimens, resulting in a lack of compliance and further symptom progression.

With respect to surgical procedures, one way to treat glaucoma is to implant a drainage device in the eye. The drainage device functions to drain aqueous humor from the anterior chamber and thereby reduce the intraocular pressure. The drainage device is typically implanted using an invasive surgical procedure. Pursuant to one such procedure, a flap is surgically formed in the sclera. The flap is folded back to form a small cavity and the drainage device is inserted into the eye through the flap. Such a procedure can be quite traumatic as the implants are large and can result in various adverse events such as infections and scarring, leading to the need to re-operate.

Current devices and procedures for treating glaucoma have disadvantages and only moderate success rates. The procedures are very traumatic to the eye and also require highly accurate surgical skills, such as to properly place the drainage device in a proper location. In addition, the devices that drain fluid from the anterior chamber to a subconjunctival bleb beneath a scleral flap are prone to infection, and can occlude and cease working. This can require re-operation to remove the device and place another one, or can result in further surgeries. In view of the foregoing, there is a need for improved devices and methods for the treatment of glaucoma.

SUMMARY

Disclosed are devices and methods for treatment of eye disease such as glaucoma. An implant is placed in the eye wherein the implant provides a fluid pathway for the flow or drainage of aqueous humor from the anterior chamber to the suprachoroidal space. The implant includes a shape change region and is implanted in the eye using a delivery system that uses a minimally-invasive procedure.

The implant described herein is designed to enhance aqueous flow through the normal outflow system of the eye with minimal to no complications. The structure can be inserted in a constrained configuration that minimizes the diameter of the implant and can return to its natural, relaxed shape after implantation in the eye to enhance retention of the device in the eye as well as improve fluid flow and prevent or reduce clogging. Any of the procedures and devices described herein can be performed in conjunction with other therapeutic procedures, such as laser iridotomy, laser iridoplasty, and goniosynechialysis (a cyclodialysis procedure).

In an embodiment, disclosed is an ocular implant including an elongate member having a flow pathway, at least one inflow port communicating with the flow pathway, and an outflow port communicating with the flow pathway. The elongate member includes a first portion formed of a braided structure and adapted to transition between a first shape when in tension and a second shape upon release of tension and a second portion formed at least partially of a non-braided structure. The elongate member is adapted to be positioned in the eye such that the inflow port communicates with the anterior chamber and the outflow port communicates with the suprachoroidal space.

In another embodiment, disclosed is an ocular implant including an elongate member having a flow pathway, at least one inflow port communicating with the flow pathway, and an outflow port communicating with the flow pathway. At least a portion of the elongate member is adapted to reversibly deform between a first shape and a second shape upon release of tension. The elongate member is adapted to be positioned in the eye such that the inflow port communicates with the anterior chamber and the outflow port communicates with the suprachoroidal space.

In an embodiment, disclosed is a method of implanting an ocular device into the eye. The method includes forming an incision in the cornea of the eye; inserting an implant having a fluid passageway through the incision into the anterior chamber of the eye while the implant is under tension. The tension maintains the implant in a first shape. The method also includes the steps of passing the implant along a pathway from the anterior chamber into the suprachoroidal space; positioning the implant in a first position such that a first portion of the fluid passageway communicates with the anterior chamber and a second portion of the fluid passageway communicates with the suprachoroidal space to provide a fluid passageway between the suprachoroidal space and the anterior chamber; and releasing the implant from tension wherein the release of tension permits the implant to transition to a second shape.

In another embodiment, disclosed is a method of implanting an ocular device into the eye that includes the steps of forming an incision in the cornea of the eye; loading on a delivery wire of a delivery device an implant having a fluid passageway. The delivery wire is adapted to impose tension to deform at least a portion of the implant from a first shape conducive to retention within the suprachoroidal space into a second shape conducive to delivery. The method also includes the steps of inserting the implant loaded on the delivery wire through the incision into the anterior chamber of the eye; passing the implant along a pathway from the anterior chamber into the suprachoroidal space; positioning the implant in a first position such that a first portion of the fluid passageway communicates with the anterior chamber and a second portion of the fluid passageway communicates with the suprachoroidal space to provide a fluid passageway between the suprachoroidal space and the anterior chamber; and releasing the implant from the delivery device wherein the release removes the tension and permits at least a portion of the implant to return to the first shape conducive to retention within the suprachoroidal space.

In an embodiment, disclosed is a system for treating an ocular disorder in a patient. The system includes an elongate member having a flow pathway, at least one inflow port communicating with the flow pathway, and an outflow port communicating with the flow pathway. The elongate member includes a first portion formed of a braided structure and adapted to transition between a first shape when in tension and a second shape upon release of tension, and a second portion formed at least partially of a non-braided structure. The elongate member is adapted to be positioned in the eye such that the inflow port communicates with the anterior chamber and the outflow port communicates with the suprachoroidal space; and a delivery device having a delivery component that removably attaches to the elongate member. The delivery component is adapted to maintain the elongate member in tension.

In another embodiment, disclosed is a system for treating an ocular disorder in a patient. The system includes an elongate member having a flow pathway, at least one inflow port communicating with the flow pathway, and an outflow port communicating with the flow pathway. At least a portion of the elongate member is adapted to reversibly deform between a first shape and a second shape. The elongate member is adapted to be positioned in the eye such that the inflow port communicates with the anterior chamber and the outflow port communicates with the suprachoroidal space. The system also includes a delivery device having a delivery component that removably couples to the elongate member. The delivery component is adapted to deform at least a portion of the elongate member into the first shape by imposing tension.

Other features and advantages should be apparent from the following description of various embodiments, which illustrate, by way of example, the principles of the invention.

BRIEF DESCRIPTION OF THE DRAWINGS

FIG. 5A shows another embodiment of an implant at least partially formed of a shape-changing material.

FIG. 5B shows the implant of FIG. 5A in an expanded state.

FIGS. 7A-7C show an exemplary mechanism for delivering the implant of FIG. 5A.

FIGS. 8A-8C show exemplary methods of manufacturing a shape-changing portion of an implant.

DETAILED DESCRIPTION

Figure 1:
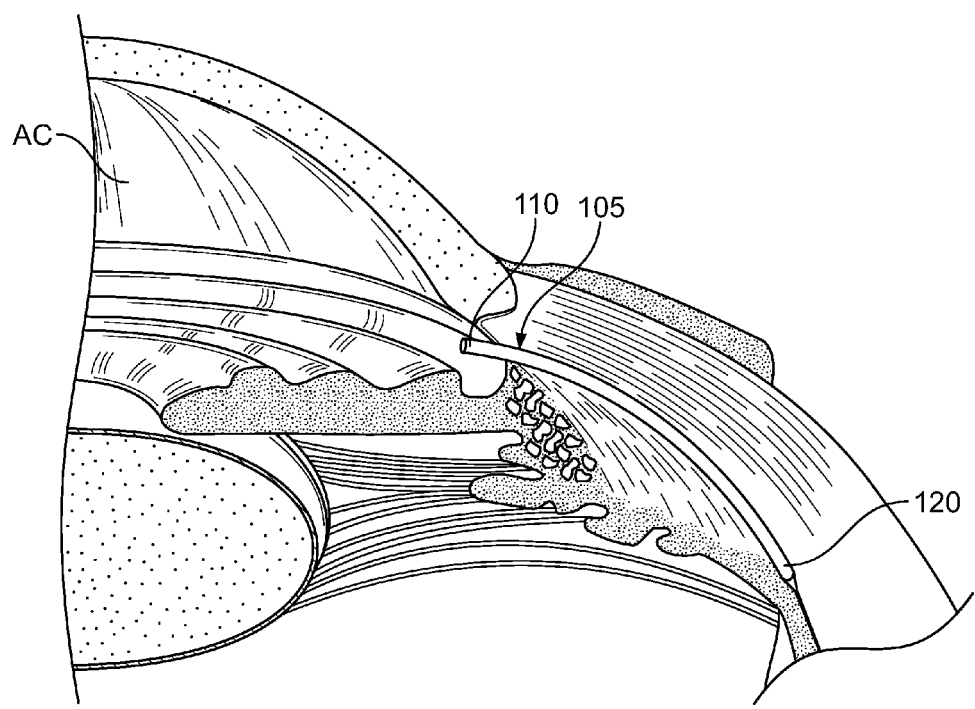
FIG. 1 is a cross-sectional, perspective view of a portion of the eye showing the anterior and posterior chambers of the eye.

FIG. 1 is a cross-sectional, perspective view of a portion of the eye showing the anterior and posterior chambers of the eye. A schematic representation of an implant 105 is positioned inside the eye such that a proximal end 110 is located in the anterior chamber AC and a distal end 120 is located in or near the suprachoroidal space (sometimes referred to as the perichoroidal space). The suprachoroidal space can include the region between the sclera and the choroid. The suprachoroidal space can also include the region between the sclera and the ciliary body. In this regard, the region of the suprachoroidal space between the sclera and the ciliary body may sometimes be referred to as the supraciliary space. The implant described herein is not necessarily positioned between the choroid and the sclera. The implant may be positioned at least partially between the ciliary body and the sclera or it may be at least partially positioned between the sclera and the choroid. The implant may also be at least partially positioned in the suprachoroidal space. In any event, the implant provides a fluid pathway between the anterior chamber and the suprachoroidal space.

In an embodiment, the implant 105 is an elongate element having one or more internal lumens through which aqueous humor can flow from the anterior chamber AC into the suprachoroidal space such as in the region between the sclera and the choroid. At least a portion of the implant is formed of a structure that is adapted to change from a first shape to a second shape. The change in shape can occur prior to, during, or after the implant is implanted in the eye, as described in more detail below. The implant 105 can have a substantially uniform diameter along its entire length, although the shape of the implant 105 can vary along its length (either before or after insertion of the implant), as described below. Moreover, the implant 105 can have various cross-sectional shapes (such as a, circular, oval or rectangular shape) and can vary in cross-sectional shape moving along its length. The cross-sectional shape can be selected to facilitate easy insertion into the eye. In one embodiment the implant is manufactured at least partially of a shape-changing material. In another embodiment, at least a portion of the implant is formed of a braided structure that is adapted to change from a first shape to a second shape.

It should be appreciated the several shape change configurations are considered herein. It should also be appreciated that features described with respect to one embodiment can be used with other embodiments described herein.

Exemplary Eye Anatomy

Figure 2:
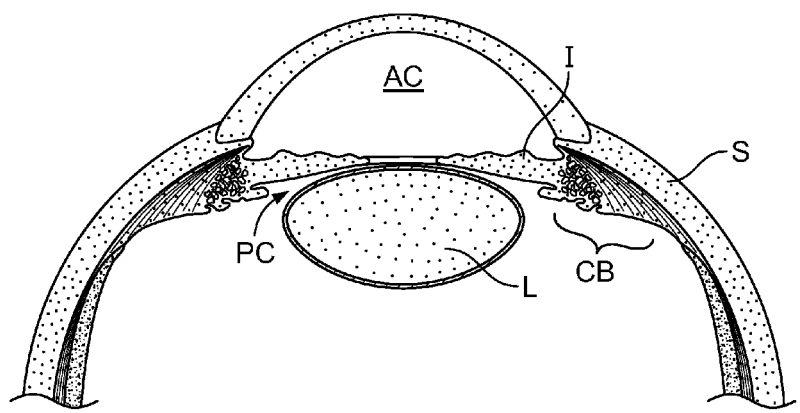
FIG. 2 is a cross-sectional view of a human eye.

FIG. 2 is a cross-sectional view of a human eye. The eye is generally spherical and is covered on the outside by the sclera S. The retina lines the inside posterior half of the eye.

The retina registers the light and sends signals to the brain via the optic nerve. The bulk of the eye is filled and supported by the vitreous body, a clear, jelly-like substance.

The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

The ciliary body CB continuously forms aqueous humor in the posterior chamber PC by secretion from the blood vessels. The aqueous humor flows around the lens L and iris I into the anterior chamber and exits the eye through the trabecular meshwork, a sieve-like structure situated at the corner of the iris I and the wall of the eye (the corner is known as the iridocorneal angle). Some of the aqueous humor filters through the trabecular meshwork into Schlemm's canal, a small channel that drains into the ocular veins. A smaller portion rejoins the venous circulation after passing through the ciliary body and eventually through the sclera (the uveoscleral route).

Glaucoma is a disease wherein the aqueous humor builds up within the eye. In a healthy eye, the ciliary processes secrete aqueous humor, which then passes through the angle between the cornea and the iris. Glaucoma appears to be the result of clogging in the trabecular meshwork. The clogging can be caused by the exfoliation of cells or other debris. When the aqueous humor does not drain properly from the clogged meshwork, it builds up and causes increased pressure in the eye, particularly on the blood vessels that lead to the optic nerve. The high pressure on the blood vessels can result in death of retinal ganglion cells and eventual blindness.

Closed angle (acute) glaucoma can occur in people who were born with a narrow angle between the iris and the cornea (the anterior chamber angle). This is more common in people who are farsighted (they see objects in the distance better than those which are close up). The iris can slip forward and suddenly close off the exit of aqueous humor, and a sudden increase in pressure within the eye follows.

Open angle (chronic) glaucoma is by far the most common type of glaucoma. In open angle glaucoma, the iris does not block the drainage angle as it does in acute glaucoma. Instead, the fluid outlet channels within the wall of the eye gradually narrow with time. The disease usually affects both eyes, and over a period of years the consistently elevated pressure slowly damages the optic nerve.

Embodiments of Shape-Change Retention Implants

Figure 3:
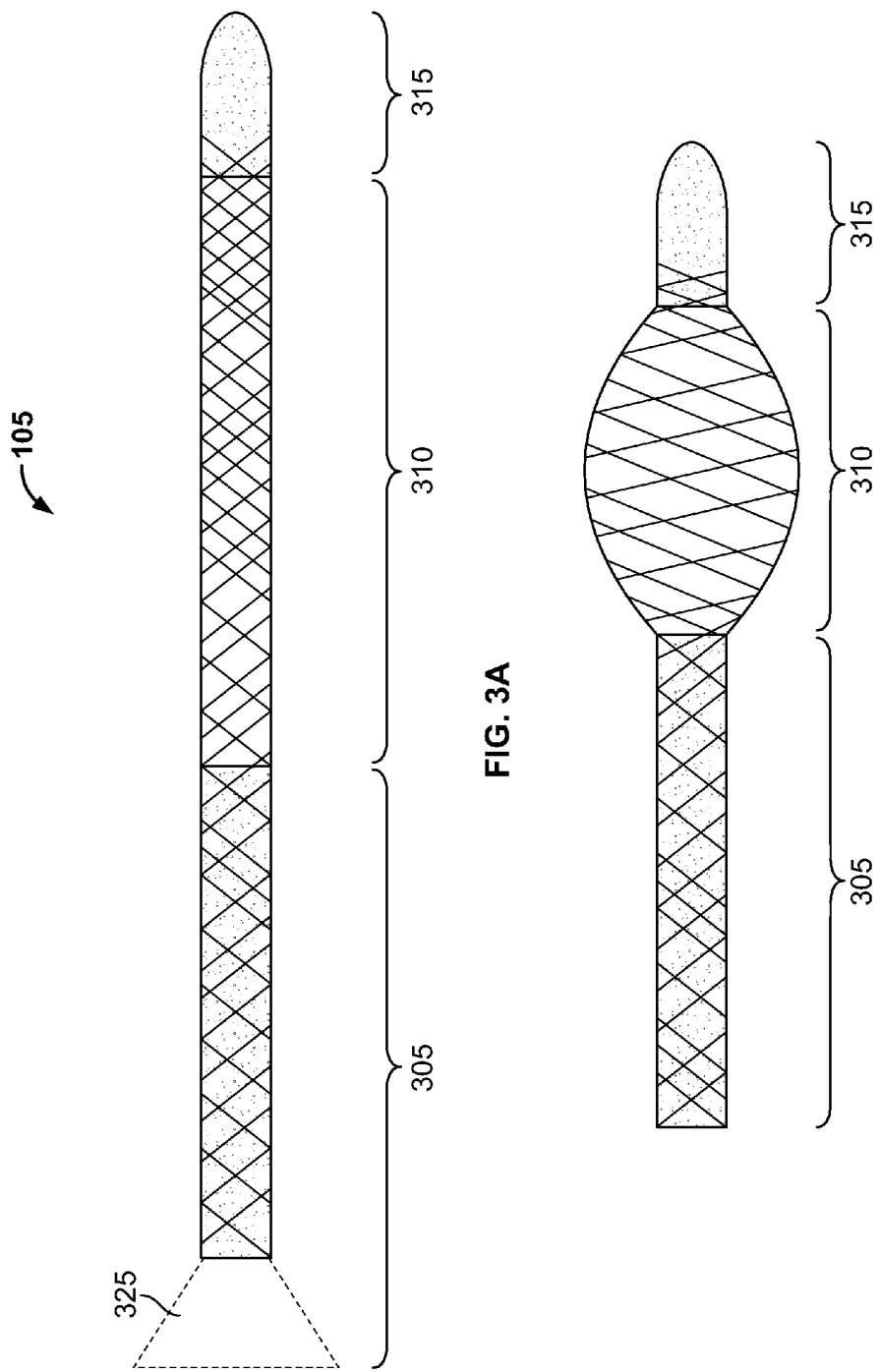
FIG. 3A shows an embodiment of an implant at least partially formed of a braided structure.
FIG. 3B shows the implant of FIG. 3A in an expanded state.

FIG. 3A shows a first embodiment of the implant 105 in an unexpanded state. As mentioned, the implant 105 is an elongate member having a proximal end, a distal end, and a structure that permits fluid (such as aqueous humour) to flow along the length of the implant such as through the implant or around the implant. In the embodiment of FIG. 3A, the implant includes at least one internal lumen having at least one opening for ingress of fluid (such as aqueous humor from the anterior chamber) and at least one opening for egress of fluid. The implant 105 can include various arrangements of openings that communicate with the lumen(s).

The internal lumen serves as a passageway for the flow of aqueous humour through the implant 105 directly from the anterior chamber to the suprachoroidal space. In addition, the internal lumen can be used to mount the implant 105 onto a delivery system, as described below. The internal lumen can also be used as a pathway for flowing irrigation fluid into the eye generally for flushing or to maintain pressure in the anterior chamber, or using the fluid to hydraulically create a dissection plane into or within the suprachoroidal space. In the embodiment of FIG. 3A, the implant 105 has a substantially uniform diameter along its entire length, although the diameter of the implant can vary along its length (either before or after expansion of the implant), as described below. Moreover, the implant can have various cross-sectional shapes (such as a circular, oval or rectangular shape) and can vary in cross-sectional shape moving along its length. The cross-sectional shape can be selected to facilitate easy insertion into the eye.

FIG. 3A shows embodiment of the implant 105 comprised of a tubular or partially tubular structure. The implant 105 is at least partially manufactured of a mesh or braided structure formed of two or more interwoven strands, fibers, or threads of material. The interwoven strands can be arranged in a pattern that forms diamond-shaped holes or openings therebetween or openings of other shapes. The braided structure can be positioned over or otherwise combined with a solid tube wherein the solid tube has an internal lumen through which fluid can travel. Thus, the braided structure and the solid tube collectively form a braid-reinforced structure.

With reference to FIG. 3A, the implant 105 has a proximal section 305, a central section 310, and a distal section 315. In an embodiment, the proximal section 305 is formed of a solid tube (with internal lumen) that is overlayed with a braided structure such that the proximal section 305 is a braid-reinforced section. In an embodiment, the central section 310 is formed entirely of a braided structure. In another embodiment, the central section 310 is partially coated with a material. The distal section 315 comprises a distal tip that is not overlayed with a braided structure or that is partially overlayed with a braided structure. The distal section 315 can have an internal lumen or it can be entirely solid with no internal lumen. The central section 310 is "open" in that the openings between the strands of the braided structure are uncovered. Thus, fluid can flow through the openings in an unimpeded manner. On the other hand, the proximal section 305 and distal section 315 are "closed" in that the solid structure blocks the openings between the strands of the braided structure, where present. The openings in the braided structure can be filled with a material or mixture of materials, such as a sponge material, to prevent unwanted tissue ingrowth into the openings when the device is implanted in the eye. The sponge material can also be filled with a drug or other material that leaks into the eye upon implantation.

The braided structure of the implant is configured to change shape, such as to expand outward, during or after implantation in the eye. The shape change can facilitate anchoring in the eye and prevent migration of the implant once it is positioned in the eye. In addition, the shape change causes the openings in the braided structure to widen, which permits increased flow through the implant and reduces the likelihood of the implant becoming clogged. During delivery of the implant 105, the openings can be positioned so as to align with predetermined anatomical structures of the eye. For example, one or more openings can align with the suprachoroidal space to permit the flow of aqueous humour into the suprachoroidal space, while another set of openings aligns with structures proximal to the suprachoroidal space, such as structures in the ciliary body or the anterior chamber of the eye.

The change in shape can be an outward expansion or can be any other change in shape, such as to change from a straightened to a non-straightened (e.g., curved or wavy) shape. The shape change can occur in a variety of manners. For example, the braided structure can be spring-loaded or biased such that the strands of the braid move relative to one another or deform so that the braid springs open to cause the openings between the strands to enlarge in size. The strands of the braid can be formed of a material, such as a spring metal or superelastic metal, that is heat or cold treated or pressure set to a desired spring-open configuration. The strands can also be formed of a polymer or can be formed of a composite (fiber-reinforced strands).

During delivery of the implant into the eye, the implant is constrained in an alternate shape and then is released to permit the implant to revert to the heat-set shape. Alternately, the spring-open action can be provided by coating the openings, the fibers, and/or the fiber cross-over locations in the braided structure with an elastomer. In another embodiment, the braided structure is at least partially formed of a shape-change material that changes shape in response to predetermined conditions, such as a change in temperature.

In another embodiment, the proximal section 305 and distal section 315 both are formed of braided structures. The central section 310 is formed of a solid structure that is overlayed or partially overlayed with a braided structure. Any of the sections can have an internal lumen that extends through the section. As in the previous embodiment, the braided sections 305 and 315 can be heat or cold treated or pressure set to a desired spring-open configuration such as an enlarged configuration. The sections 305 and/or 315 can transition to an expanded shape. It should be appreciated that the implant can have various combinations and geometric arrangements of solid, braid reinforced structures and braided structures.

In any of the embodiments, the ends of the braided structure can be gathered and held in place by an adjacent solid structure, such as a bullet nose at the distal tip of the implant or a tube at the proximal tip.

FIG. 3B shows the implant of FIG. 3A in an expanded state. The "open" central section 310 has enlarged to an expanded state. In an embodiment, the shape of the proximal section 305 and distal section 315 do not undergo expansion and are unchanged. Alternately, the proximal and distal sections have undergone some expansion or other shape change (e.g., contraction or expansion) but the amount of expansion is less than the expansion of the braided central section 310. The presence of the solid portions in the proximal and distal sections keeps the braided structure if present, in those sections from expanding outward. When implanted in the eye, fluid can pass into the implant 105 via the internal lumen of the proximal section 305. Fluid travels into the internal lumen of the central section 310 (toward the distal section 315) where the fluid drains though the openings in the braided structure of the central section.

Figure 4:
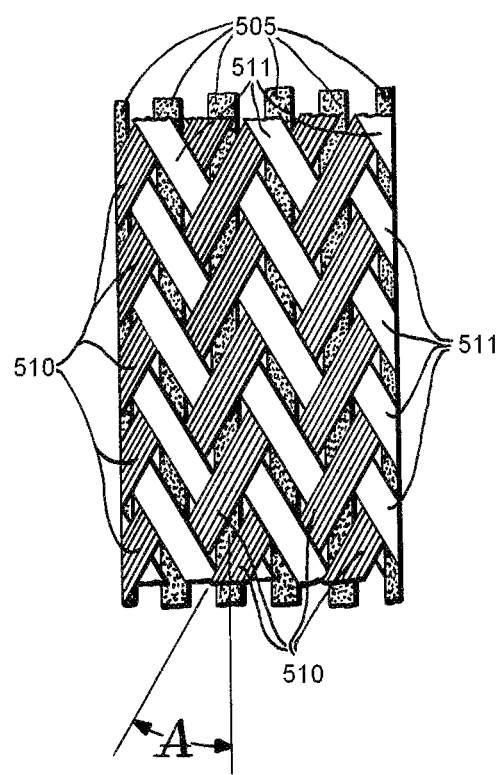
FIG. 4 shows an exemplary embodiment of a section of the braided structure of the implant of FIG. 3A.

The implant 105 can have any of a variety braided structures and non-braided structures that are connected and arranged in various manners. FIG. 4 shows an exemplary embodiment of a section of braided structure. It should be appreciated that the structure of FIG. 4 is an example and that the braided structure can have other arrangements. In the exemplary embodiment, the braided structure is a triaxial braid structure having a plurality of axial members 505 that extend generally parallel to the longitudinal axis of the implant. The braided structure forms a three dimensional tube shape. A plurality of cross-members 510, 511 are arranged diagonal to the axial members 505 at a braiding angle A relative to the axes of the axial members 505. In cross-section, the axial members 505 and cross-members 510, 511 collectively form a cylinder or another three-dimension shape having an internal lumen. The axial members 505 are elastic (e.g., formed of an elastomer) while the cross-members 510,511 are formed of a high-strength material. The braids can be arranged in a variety of patterns including, for example, a one-over pattern, diamond pattern, non-diamond pattern. The axial members or cross-members can be flat banded fibers. That is, the members can have flat outer surfaces and can be rectangular in cross-section.

FIG. 5A shows another embodiment of a shape change implant. As with the previously described embodiment, the implant 105 is an elongate member that has a proximal region 305, a distal region 315, and a generally tubular or partially tubular structure that permits fluid (such as aqueous humor) to flow along the length of the implant such as through or around the implant. The implant 105 includes at least one internal lumen having at least one opening for ingress of fluid (such as aqueous humor from the anterior chamber) and at least one opening for egress of fluid. The implant 105 can include various arrangements of openings 125 that communicate with the lumen(s). The openings 125 in the implant 105 can be filled with a material or mixture of materials, such as a sponge material, to prevent unwanted tissue ingrowth into the openings 125 when the device is implanted in the eye. The sponge material can also be filled with a drug or other material that leaks into the eye upon implantation.

As with the previous embodiment, the openings 125 of the implant can be positioned so as to align with predetermined anatomical structures of the eye. For example, one or more openings 125 can align with the suprachoroidal space to permit the flow of aqueous humor into the suprachoroidal space, while another set of openings 125 can be positioned within structures proximal to the suprachoroidal space, such as structures in the ciliary body or the anterior chamber of the eye.

In the embodiment shown in FIG. 5A, the implant 105 is at least partially manufactured of a shape changing material. In an embodiment, the distal region 315 includes a shape changing portion. The shape changing portion of the implant 105 is configured to change shape upon insertion in the eye, for example the implant 105 can bow outward. The shape change can facilitate anchoring and retention in the eye and prevent migration of the implant 105 once it is in position. In addition, the shape change can cause the openings 125 to widen, which permits increased flow through the implant 105 and reduces the likelihood of the implant 105 becoming clogged.

During delivery of the implant 105 into the eye, the implant is constrained in a first shape conducive to insertion in the eye (see, for example, FIG. 5A). The first shape can be a relatively straight configuration. The implant 105 is then released to permit the implant to revert to a second shape conducive to retention of the implant in the eye (see, for example, FIG. 5B). The first shape can be a stressed or constrained shape whereas the second shape can be an unstressed or relaxed shape of the implant. The change from a first to a second shape can be an outward bowing as shown in the figures. The change in shape can be any other change in shape, such as to change from a straightened to a non-straightened (e.g., curved or wavy) shape or from a narrow to an expanded shape.

The shape change can occur in a variety of manners. For example, the implant can be manufactured of a thermoplastic elastomer (TPE) that is capable of being reversibly deformed as discussed in more detail below. The implant 105 can be heat-set such that it is has a tendency to return from the first, constrained shape desired during delivery to the second, relaxed shape desired for retention and fluid passage. The implant 105 maintains the first shape when the implant is constrained in some manner such as by a guidewire or other delivery mechanism or device having a lower flexibility or elasticity than the shape changing portion of the implant 105. When the implant 105 is at or near the desired location in the eye, the constraint(s) can be removed or the implant released, such as by removal of the guidewire or other structure, so that the implant transitions or changes toward the second, retention shape such as shown in FIG. 5B.

Additional Implant Features

The implants described herein can include additional features to improve their effectiveness in draining fluid from the anterior chamber to the suprachoroidal space. For example, the implants described herein can be equipped with a collar 325 disposed on or near the proximal end of the implant. As shown in FIGS. 3A and 5A, the collar 325 is shown in phantom lines to indicate that the collar 325 is optional. The collar 325 can be formed of the same material as the rest of the implant 105 or a different material. The collar 325 can have various shapes including a funnel shape such that the collar 325 provides a relatively wide opening that communicates with the internal lumen of the implant 105. In an embodiment, the collar 325 is formed of a braided structure and is funnel shaped such that the collar 325 provides a relatively wide opening that communicates with the internal lumen of the proximal section 305. In another embodiment, the collar 325 is formed of a braid-reinforced plastic material. In another embodiment, the collar 325 is formed of plastic but is not braid-reinforced.

The implants described herein can also include additional structural features in addition to the shape change region that assist in anchoring or retaining the implant in the eye. For example, the implant can include one or more retaining or retention structures, such as flanges, protrusions, wings, tines, or prongs, that lodge into the surrounding eye anatomy to retain the implant in place and prevent the implant from moving further into the suprachoroidal space. The retention features can also provide regions for fibrous attachment between the implant and the surrounding eye anatomy.

The additional retention structures can be deformable or stiff and can be made of various biocompatible materials such as described above. For example, the additional retention structures can be made from thin 0.001" thick polyimide, which is flexible, thin 0.003" silicone elastomer which is also flexible, or stainless steel or Nitinol. Alternatively, the additional retention structures could be rings of polyimide. It should be appreciated that other materials can be used to make the additional retention structures. The shape of additional retention structures can vary. Alternatively, the additional retaining features can be manufactured as separate parts and assembled onto the implant as described above. They can fit into grooves, holes or detents in the body of the implant to lock them together. If the additional retaining features are constructed from hairs or sutures, they can be threaded or tied onto the implant. Alternatively, the additional retaining features can be overmolded onto the implant via an injection molding process. In an embodiment, the entire implant and additional retention features can be injection molded in one step. In another embodiment, the additional retaining features can be formed into the implant with a post-processing step such as such as those described in more detail below.

The implants described herein can have one or more features that aid in properly positioning the implant in the eye. For example, the implants can include one or more visual, tomographic, echogenic, or radiopaque markers along the length to assist the user in positioning the desired portion of the implant within the anterior chamber and the desired portion within the suprachoroidal space. In using the markers to properly place the implant, the implant is inserted in the suprachoroidal space, until the marker is aligned with a relevant anatomic structure, for example, visually identifying a marker on the anterior chamber portion of the implant that aligns with the trabecular meshwork, or scleral spur, such that an appropriate length of the implant remains in the anterior chamber. Under ultrasound, an echogenic marker can signal the placement of the device within the suprachoroidal space. Any marker can be placed anywhere on the device to provide sensory feedback to the user on real-time placement, confirmation of placement or during patient follow up. Further, the implants and delivery system can employ alignment marks, tabs, slots or other features that allow the user to know alignment of the implant with respect to the delivery device.

Shape Change of Implant

As described above, the implants described herein are configured to change shape, such as to bow or expand outward, during or after implantation in the eye. The material of the implant 105 can be reversibly deformed such that it can take on a narrow profile (e.g. such as shown in FIGS. 3A and 5A) that is suitable for insertion through a small opening and then return to the retention shape (e.g. such as shown in FIGS. 3B and 5B). The implant maintains the alternate, insertion shape when it is under a tension or constrained in some manner. When the implant is at or near the desired location in the eye, the constraint(s) can be removed or released so that the implant reverts or transitions back to a relaxed retention shape.

Figure 6A:
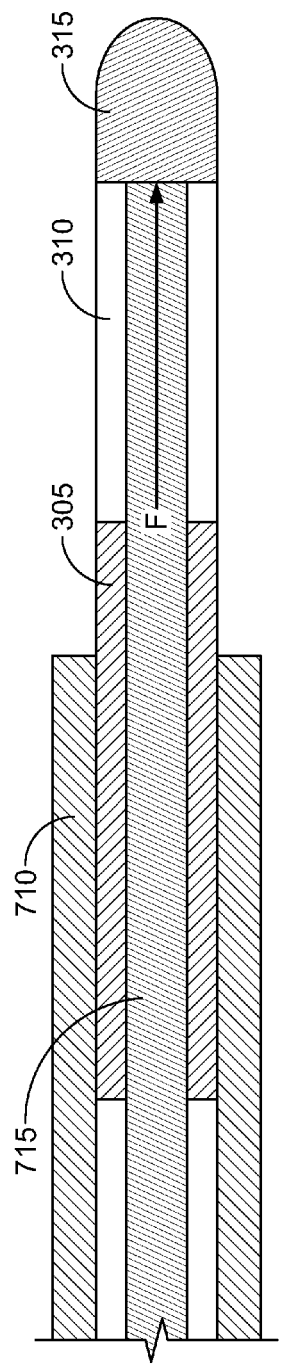
FIGS. 6A-6C show an exemplary mechanism for delivering the implant of FIG. 3A.

FIG. 6A shows one embodiment of a cross-sectional view of an implant 105 attached to a distal region of a delivery system. The entire delivery system is described in more detail below. The delivery system includes a constraining structure, such as a sheath 710, that is sized and shaped to receive the proximal section 305 of the implant. The sheath 710 removably attaches to and constrains the proximal section 305 such as via a press-fit or any other type of mechanical attachment.

The delivery system also includes an elongate delivery wire 715 that is sized and shaped to be inserted longitudinally through the internal lumen of the implant 105. The delivery wire 715 is more rigid than the implant 105 such that it constrains the implant 105 in the straighter, insertion configuration. Although the delivery wire 715 is more rigid than the implant, it still remains flexible and compliant enough to allow for blunt dissection such as between the tissue layers of the sclera and choroid and able to follow the natural curve of the inner scleral wall. It should be appreciated that other structures can be used to constrain the implant 105.

FIG. 6A shows the sheath 710 attached to the proximal section 305 of the implant such that the sheath 710 fits over the proximal section 305 to constrain it to the size of the inner diameter of the sheath 710. With the proximal section 305 constrained, the delivery wire 715 applies a distally-directed force F against the distal section 315 such that the implant is in tension. The force F against the distal section 315 combined with the implant's attachment to the proximal section 305 cause the braided central section 310 to be in a stretched state of reduced diameter and increased length relative to a non-stretched state. In other words, the delivery system constrains and maintains the implant 105 in the first shape shown in FIG. 3A.

Figure 6B:
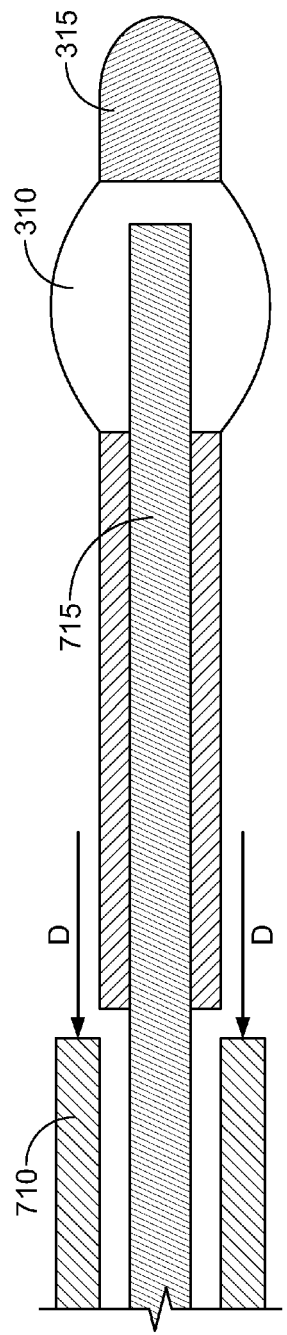

FIG. 6B shows the delivery system after the sheath 710 has been retracted distally (represented by the arrows D) relative to the implant and thereby detached from the proximal section 305 of the implant 105. While the sheath 710 was attached to the implant, the sheath 710 and the delivery wire 715 collectively maintained the implant in a state of tension. With the sheath 710 no longer constraining the proximal section 305 in a state of tension, the implant 105 is now free to move toward its expanded shape. The braided central section 310 moves toward its expanded shape such that the central section 310 changes to a bulbous shape. As this occurs, the distal section 315 moves away from the distal tip of the delivery wire 715 (or vice-versa), as shown in FIG. 6B.

Figure 6C:
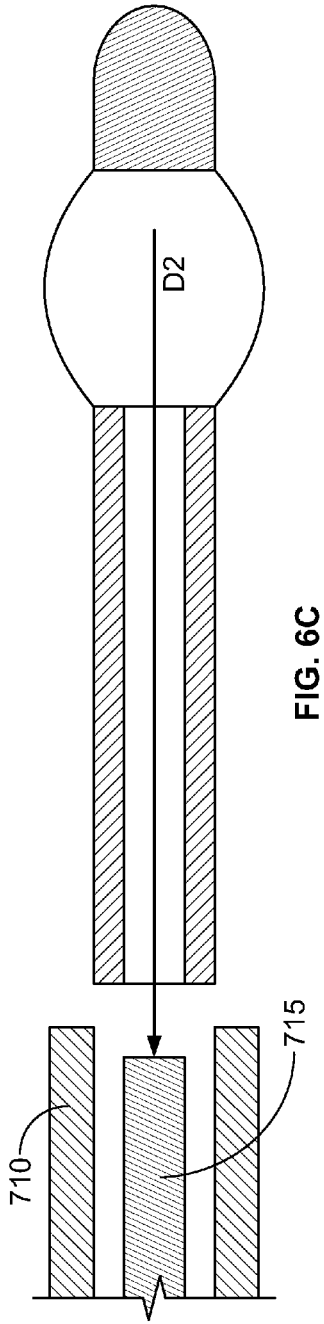

In a next step, shown in FIG. 6C, the delivery wire 715 is retracted distally (as represented by the arrow D2) relative to the implant 105 such that the delivery wire 715 and the sheath 710 are both entirely disengaged from the implant 105. The implant 105 is now entirely free to transition toward its second retention shape. As discussed above, the second shape may be of smaller length but greater diameter than the first shape.

FIG. 7A shows a schematic, cross-sectional view of another embodiment of an implant 105 attached to a distal region of a delivery system inserted from the anterior chamber AC into the suprachoroidal space SC. Like the previous embodiment, the delivery system can include a constraining structure such as a sheath 710 that is sized and shaped to receive a portion of the proximal section 305 of the implant. For example, the sheath 710 can removably attach to the proximal section 305 such as via a press-fit or any other type of mechanical attachment. In this regard, the sheath 710 may have an internal lumen into which the implant fits such that the implant is removably constrained in the sheath 710. Other means of removably attaching the sheath 710 to the implant can be used.

The delivery system also includes an elongate delivery wire 715 that is sized and shaped to be inserted longitudinally through the internal lumen of the implant 105. The delivery wire 715 is more rigid than the implant 105 such that it constrains the implant 105 in the straighter, insertion configuration. Although the delivery wire 715 is more rigid than the implant, it still remains flexible and compliant enough to allow for blunt dissection for example between the tissue layers of the sclera and choroid and able to follow the natural curve of the inner scleral wall. It should be appreciated that other structures can be used to constrain the implant 105.

FIG. 7B shows the delivery system after the delivery wire 715 has been retracted proximally (represented by the arrow P) relative to the implant 105. With the delivery wire 715 no longer constraining the distal region 315 of the implant in a state of tension in the generally straight insertion configuration, the distal region 315 of the implant 105 is now free to move toward the retention shape. In the case of FIGS. 7B and 7C, the retention shape is a wavy or bowed shape. In any of the embodiments described herein, the shape of the implant at body temperature does not deform beyond the yield during implantation.

Manufacture of Shape Change Implants

In an embodiment, the implant 105 has a longitudinal stiffness or column strength sufficient to permit the implant 105 to be inserted into the suprachoroidal space such that the distal tip of the implant 105 tunnels through certain eye tissue (such as the ciliary body) and between certain eye tissues (such as between the sclera and the choroid or between the sclera and the ciliary body) without structural collapse or structural degradation of the implant 105. In addition, the surface of the inner lumen is sufficiently smooth relative to the delivery device (described in detail below) to permit the implant 105 to slide off of the delivery device during the delivery process. In an embodiment, the column strength is sufficient to permit the implant to tunnel through certain eye tissues into the suprachoroidal space without any structural support from an additional structure such as a delivery device.

The dimensions of the implants described herein can vary. In an exemplary embodiment, the implant has a length in the range of 0.1" to 0.75" and an inner diameter for a flow path in the range of 0.002" to 0.015". In an embodiment, the inner diameter is 0.012", 0.010", or 0.008". In the event that multiple implants are used, and for example each implant is 0.1", the fully implanted device can create a length of 0.2" to 1.0", although the length can be outside this range. An embodiment of the implant is 0.250" long, 0.012" in inner diameter, and 0.015" in outer diameter. One embodiment of the implant is 0.300" long.

The implants described herein including their shape changing portion(s) can be made of various biocompatible materials. In an embodiment, the implants can be manufactured of synthetic polymeric materials that show reversible extension and can be deformed repeatedly such that they return to their "original" heat-set shape when the stress is released. The reversible deformation of the implant, even at higher body temperatures, is a desirable characteristic.

The implant or portion(s) thereof can be made of various materials, including, for example, thermoplastic elastomers, polyimide, Nitinol, platinum, stainless steel, molybdenum, or any other suitable polymer, metal, metal alloy, or ceramic biocompatible material or combinations thereof. The material of manufacture is desirably selected to have material properties suited for the particular function of the implant or portion thereof.

Other materials of manufacture or materials with which the implant can be coated or manufactured entirely include silicone, thermoplastic elastomers (HYTREL, KRATON, PEBAX), certain polyolefin or polyolefin blends, elastomeric alloys, polyurethanes, thermoplastic copolyester, polyether block amides, polyamides (such as Nylon), block copolymer polyurethanes (such as LYCRA). Some other exemplary materials include fluoropolymer (such as FEP and PVDF), polyester, ePTFE (also known as GORETEX), FEP laminated into nodes of ePTFE, acrylic, low glass transition temperature acrylics, silver coatings (such as via a CVD process), gold, polypropylene, poly(methyl methacrylate) (PMMA), PolyEthylene Terephthalate (PET), Polyethylene (PE), PLLA, parylene, PEEK, polysulfone, polyamideimides (PAI) and liquid crystal polymers. It should also be appreciated that stiffer polymers can be made to be more compliant by incorporating air or void volumes into their bulk, for example, PTFE and expanded PTFE. In order to maintain a low profile, well-known sputtering techniques can be employed to coat the implant. Such a low profile coating would accomplish a possible goal of preventing migration while still allowing easy removal if desired.

The implant can have braids or wires reinforced with polymer, Nitinol, or stainless steel braid or coiling or can be a co-extruded or laminated tube with one or more materials that provide acceptable flexibility and hoop strength for adequate lumen support and drainage through the lumen.

The implant can also be manufactured of, coated or layered with a material that expands outward once the implant has been placed in the eye. The expanded material fills any voids that are positioned around the implant. Such materials include, for example, hydrogels, foams, lyophilized collagen, or any material that gels, swells, or otherwise expands upon contact with body fluids.

Any of the embodiments of the implants described herein can be coated on the inner or outer surface with one or more drugs or other materials, wherein the drug or material maintains the patency of the lumen or encourages in-growth of tissue to assist with retention of the implant within the eye or to prevent leakage around the implant. The drug can also be used for disease treatment. The implant can also be coated on its inner or outer surface with a therapeutic agent, such as a steroid, an antibiotic, an anti-inflammatory agent, an anti-coagulant, an anti-glaucomatous agent, an anti-proliferative, or any combination thereof. The drug or therapeutic agent can be applied in a number of ways as is known in the art. Also the drug can be embedded in another polymer (nonabsorbable or bioabsorbable) that is coated on the implant.

The shape change portion of the implant can be formed by one or more post-processing steps. Thermoplastic materials, including thermoplastic elastomers (TPEs), are characterized by labile cross-links that are reversible and can be broken when melted. This property of TPEs makes them easy to use from a manufacturing standpoint. The shape changing portion(s) of a thermoplastic implant can be processed by engineering the cross-links such as through heat, flaring, thermo-molding, pressure, chemicals or radiation such as electron beam exposure, gamma-radiation or UV light. Thermosets and cross-linked sets can also be used.

FIGS. 8A-8C show various post-processing steps used to create shape changing portions in an implant. FIG. 8A shows an embodiment in which the shape changing portion of the implant 105 is manufactured by a heating-molding-cooling series of steps to create an implant of a desired retention shape. The implant 105 can be made of a thermally-stimulated, shape-memory polymer, for example thermoplastic PVDF. Polymer pellets are extruded through a mold to form an elongate, hollow tube. At least a portion of the tubular implant is exposed again to heat, such as a heated mandrel M that heats a portion of the implant 105, to a temperature above the $T_g$ (glass transition temperature) of the material such that it goes from a rigid, glassy modulus to the rubbery modulus. Once in the rubbery modulus, the implant 105 can be deformed as desired, for example a funnel-shaped collar 325 formed in the proximal portion or an s-shaped curve in the distal portion 315. The implant 105 can then be cooled below the $T_g$. Upon cooling, the implant will retain this curved shape yet due to the flexible nature of the polymer, stress can be applied to the implant (e.g. inserting a delivery wire through the internal lumen) to temporarily change the shape of the implant to a different shape. As described above, upon removal of the constraint (e.g. removal of the delivery wire), the implant 105 will reversibly deform back into the "retention" shape.

The ability to melt and process the material of the implant is useful from a manufacturing stand-point, but can limit a material's use in elevated temperatures (i.e. inside the human body). Therefore, post-processing steps can also be used to overcome this limitation so that the implant can be used at and even above the melting point of the material without changing the properties of the material or the dimensions of the implant. For example, cross-linking thin-wall extrusion implants imparts stiffness to the implant while retaining the elastomeric properties of the material of which it is made. The end result is high durability within a wide range of temperatures and/or pressures.

Other cross-linking techniques include exposing the extruded implant to radiation (UV, gamma, or electron beam) or through a chemical process using, for example, peroxide or silane. The reactions produced by cross-linking depend on the particular material, the presence of modifying agents, and variables in processing, such as the level of irradiation. FIGS. 8B and 8C show schematics of exemplary post-processing steps in which cross-linking is induced by exposure of at least a portion of the implant to radiation, such as UV, gamma or electron beam radiation to generate thermal memory in an implant. A portion of the implant that is not cross-linked can be covered with an appropriate shield S.

With respect to the braided implant embodiment, the solid proximal and distal sections of the implant can be cast, coated (e.g., dip-coated, vapor-coated, or powder-coated), bonded, trapped (i.e., sandwiched) or otherwise attached into or onto the braided structure. In an embodiment, at least a portion of the implant is reaction cast around reinforcing wire. The strands of the braided portions of the implant can be joined to form a bulb or funnel shape, such as by welding or cold working the strands or by bonding the strands in epoxy or other matrix glues. In addition, the strands can be knotted, encapsulated with a heat shrink, insert injection molded, diffusion bonded, solvent welded, etc. The fiber cross-overs can also be crimp-set during the braiding process.

Implant Delivery System

Figure 9:
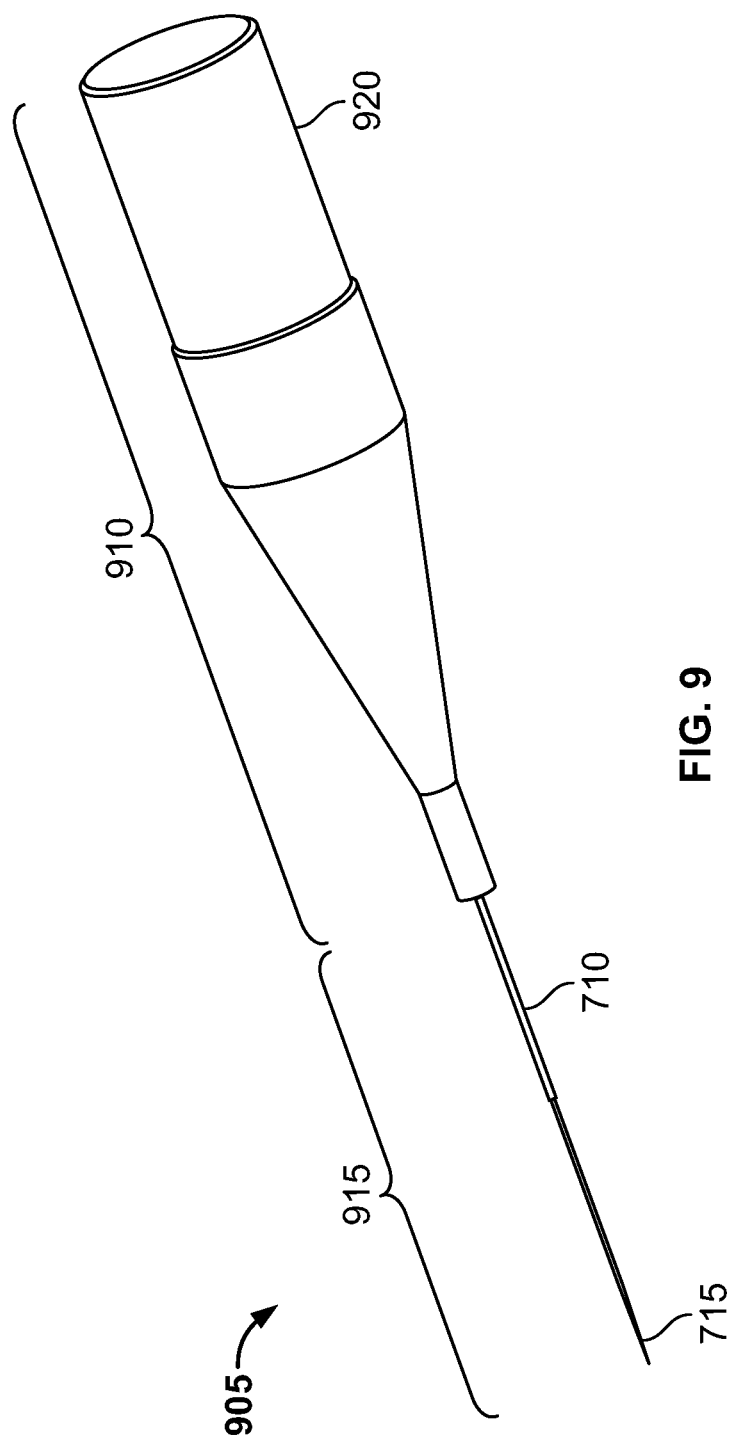
FIG. 9 shows an exemplary delivery system that can be used to deliver an implant into the eye.

There are now described devices and methods for delivering and deploying implant described herein into the eye. In an embodiment, a delivery system is used to deliver the implant into the eye such that the implant provides fluid communication between the anterior chamber and the suprachoroidal space. FIG. 9 shows an exemplary delivery system 905 that can be used to deliver the implant into the eye. It should be appreciated that the delivery system 905 is exemplary and that variations in the structure, shape and actuation of the delivery system 905 are possible.

The delivery system 905 includes a handle component 910 that controls an implant placement mechanism, and a delivery component 915 that removably couples to the implant for delivery of the implant into the eye. The delivery component 915 includes an elongate delivery wire 715 (which was previously discussed above) that is sized and shaped to be inserted longitudinally through the implant. In an embodiment, the diameter of the delivery wire 715 is at least about 0.0017". In another embodiment, the diameter of the delivery wire 715 is at least about 0.009". In one embodiment, the delivery wire 715 has a sharpened distal tip although it can also be blunt. The delivery wire 715 can have a cross-sectional shape that complements the cross-sectional shape of the internal lumen of the implant to facilitate mounting of the implant onto the delivery wire 715. The delivery wire 715 can be straight or it can be can be curved along all or a portion of its length in order to facilitate proper placement through the cornea. The delivery wire 715 is generally more rigid than the implant 105 such that it constrains the implant 105 in the straighter, insertion configuration. Although the delivery wire 715 is more rigid than the implant, it still remains flexible and compliant enough to allow for blunt dissection such as between the tissue layers of the sclera and choroid or the sclera and the ciliary body and able to follow the natural curve of the inner scleral wall.

The outer diameter of the delivery wire can be selected and optimized based on the material and flexibility of the material used for the delivery wire. A delivery wire made of nitinol, for example, can have an outer diameter of about 0.009 inches. Nitinol is a superelastic metal that is quite bendable yet is stiff enough to be pushed through the iris root and the ciliary body to reach to and hug the curve of the inner scleral wall during blunt dissection along the boundary between the sclera and the tissues adjacent to the inner scleral wall. When combined with other features of the delivery wire, for example a blunt tip, a nitinol delivery wire having an outer diameter of about 0.009 inches can be used to gently dissect the tissue layers while avoiding tunneling or piercing one or both the inner scleral wall and choroid. Stainless steel spring wire is another material that could be used for the delivery wire. Stainless steel wire is generally slightly stiffer than nitinol. Thus, the outer diameter of a delivery wire made of stainless steel wire may need to be somewhat smaller than the outer diameter for a delivery wire made of nitinol in order to achieve the same performance during blunt dissection. In an embodiment, the delivery wire has an outer diameter of about 0.0017 inches. It should be appreciated that for a given material's flexibility, the optimum outer diameter of the delivery wire can be determined and extrapolated for a delivery wire of a different material having a different degree of flexibility. Other materials considered for the delivery wire include compliant flexible wires made from a polymer or a polymer composite wire reinforced with high-strength fibers.

A variety of parameters including the shape, material, material properties, diameter, flexibility, compliance, pre-curvature and tip shape of the delivery wire 715 can impact the performance of the delivery wire 715 during gentle, blunt tissue dissection. It may be important that the delivery wire 715 be able to penetrate certain tissues while avoid penetration of other tissues. For example, in an embodiment, it is desirable that the delivery wire 715 be capable of penetrating the iris root or the ciliary body. The same delivery wire 715 would beneficially be incapable of penetrating the scleral spur or inner wall of the sclera such that it can gently dissect between the tissue boundaries adjacent to the inner wall of the sclera. It should also be appreciated that the column strength of the implant can be sufficient to permit the implant to tunnel through certain eye tissues into the suprachoroidal space without any structural support from an additional structure such as a delivery wire.

The delivery component 915 also includes a sheath 710 positioned axially over the delivery wire 715. The sheath 710 can be coupled to the implant during delivery to maintain or assist in maintaining the implant in an insertion configuration, as discussed above. With reference still to FIG. 9, the handle component 910 of the delivery system 905 can be actuated to control delivery of the implant. In this regard, the handle component 910 includes an actuator 920 that can be actuated to cause relative, sliding movement between the delivery wire 715 and the sheath 710. For example, the actuator 920 can be manipulated to cause the delivery wire 715 to withdraw proximally relative to the sheath 710. The proximal direction is represented by the arrow P in FIG. 7B.

As mentioned the delivery wire 715 is sized to fit through the lumen in the implant 105 such that the implant 105 can be mounted on the delivery wire 715. In an embodiment, the delivery wire 715 can be coated such that a press-fit between the implant 105 and the delivery wire 715 is possible. For example, the delivery wire 715 or a portion of the delivery wire 715 can be coated with a polymer or other compliant material in order to retain the implant on the delivery wire 715 during implantation and prevent inadvertent release of the implant within the eye.

Exemplary Methods of Delivery and Implantation

An exemplary method of delivering and implanting the implant into the eye is now described. In general, the implant is implanted using a delivery system by entering the eye through a corneal incision and penetrating the iris root or a region of the ciliary body or the iris root part of the ciliary body near its tissue border with the scleral spur to create a low-profile, minimally-invasive blunt dissection in the tissue plane, for example between the sclera and the ciliary body or between the sclera and the choroid. The implant is then positioned in the eye so that it provides fluid communication between the anterior chamber and the suprachoroidal space.

Figure 10:
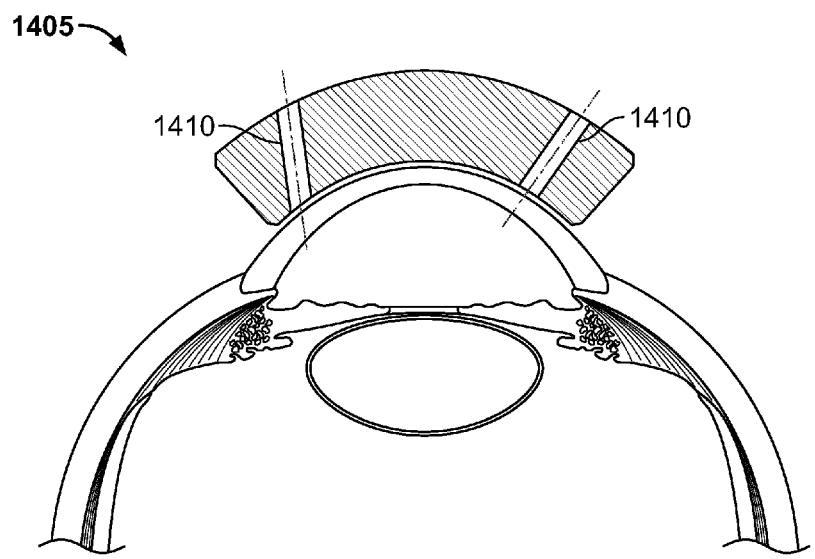
FIG. 10 shows a cross-sectional view of the eye and a viewing lens.

FIG. 10 shows a cross-sectional view of the eye. A viewing lens 1405 (such as a gonioscopy lens represented schematically in FIG. 10) is positioned adjacent the cornea. The viewing lens 1405 enables viewing of internal regions of the eye, such as the scleral spur and scleral junction, from a location in front of the eye. An operator can use the viewing lens 1405 during delivery of the implant into the eye. The viewing lens 1405 can have a shape or cutout that permits the surgeon to use the viewing lens 1405 in a manner that does not cover or impede access to the corneal incision. Further, the viewing lens 1405 can act as a guide through which a delivery system 905 can be placed to predetermine the path of the device as it is inserted through the cornea. The viewing lens 1405 can optionally include one or more guide channels 1410 that are sized to receive the delivery portion 915 of the delivery system 905. It should be appreciated that the locations and orientations of the guide channels 1410 in FIG. 10 are merely exemplary and that the actual locations and orientations can vary depending on the angle and location where the implant 105 is to be delivered. It should also be appreciated that a viewing lens need not be used.

An endoscope can also be used during delivery to aid in visualization. For example, a twenty-one to twenty-five gauge endoscope can be coupled to the implant during delivery such as by mounting the endoscope along the side of the implant or by mounting the endoscope coaxially within the implant. Ultrasonic guidance can be used as well using high resolution bio-microscopy, OCT and the like. Alternatively, a small endoscope can be inserted though a second limbal incision in the eye to image the tissue during the procedure.

In an initial step, one or more implants 105 are mounted on the delivery system 905 for delivery into the eye. The implant 105 can be mounted on the delivery system 905 such as by inserting a delivery wire 715 through the flow pathway of the implant. The eye can be viewed through the viewing lens 1405 or other viewing means such as is described above, in order to ascertain the location where the implant 105 is to be delivered. At least one goal is to deliver the implant 105 in the eye so that it is positioned such that the internal lumen of the implant provides a fluid pathway between the anterior chamber and the suprachoroidal space.

Figure 11:
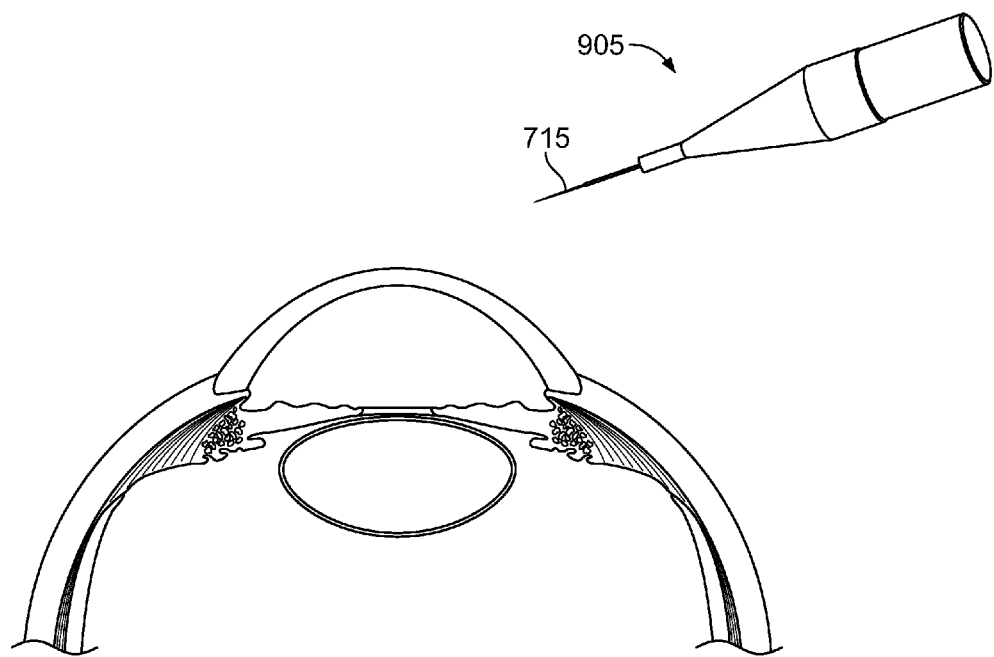
FIG. 11 shows the delivery system positioned for penetration into the eye.

With reference to FIG. 11, the delivery system 905 is positioned such that the distal tip of the delivery wire 715 or the implant 105 itself can penetrate through the cornea. In this regard, an incision is made through the eye, such as within the limbus of the cornea. In an embodiment, the incision is very close to the limbus, such as either at the level of the limbus or within 2 mm of the limbus in the clear cornea. The delivery wire 715 can be used to make the incision or a separate cutting device can be used. For example, a knife-tipped device or diamond knife can be used to initially enter the cornea. A second device with a spatula tip can then be advanced over the knife tip wherein the plane of the spatula is positioned to coincide with the dissection plane. Thus, the spatula-shaped tip can be inserted into the suprachoroidal space with minimal trauma to the eye tissue. As described above, the dynamics of the delivery wire 715 such as material, material properties, dimensions, compliance, flexibility etc. contribute in part to the blunt dissection of the eye tissue and ensure that the implantation pathway follows the natural pathway between tissue layers, for example between tissue layers such as the sclera and choroid.

The corneal incision has a size that is sufficient to permit passage of the implant therethrough. In this regard, the incision can be sized to permit passage of only the implant without any additional devices, or be sized to permit passage of the implant in addition to additional devices, such as the delivery device or an imaging device. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision. For clarity of illustration, the drawing is not to scale and the viewing lens 1405 is not shown in FIG. 11, although the applier can be guided through one or more guide channels in the viewing lens.

The delivery wire 715 can approach the iris root IR from the same side of the anterior chamber AC as the deployment location such that the applier (e.g. delivery wire) does not have to be advanced across the iris. Alternately, the applier can approach the insertion location from across the anterior chamber AC such that the applier is advanced across the iris and/or the anterior chamber toward the opposite iris root. The delivery wire 715 can approach the iris root IR along a variety of pathways. The delivery wire 715 does not necessarily cross over the eye and does not intersect the center axis of the eye. In other words, the corneal incision and the location where the implant is implanted at the iris root can be in the same quadrant (if the eye is viewed from the front and divided into four quadrants). Also, the pathway of the implant from the corneal incision to the iris root desirably does not pass through the centerline of the eye to avoid interfering with the pupil.

Figure 12:
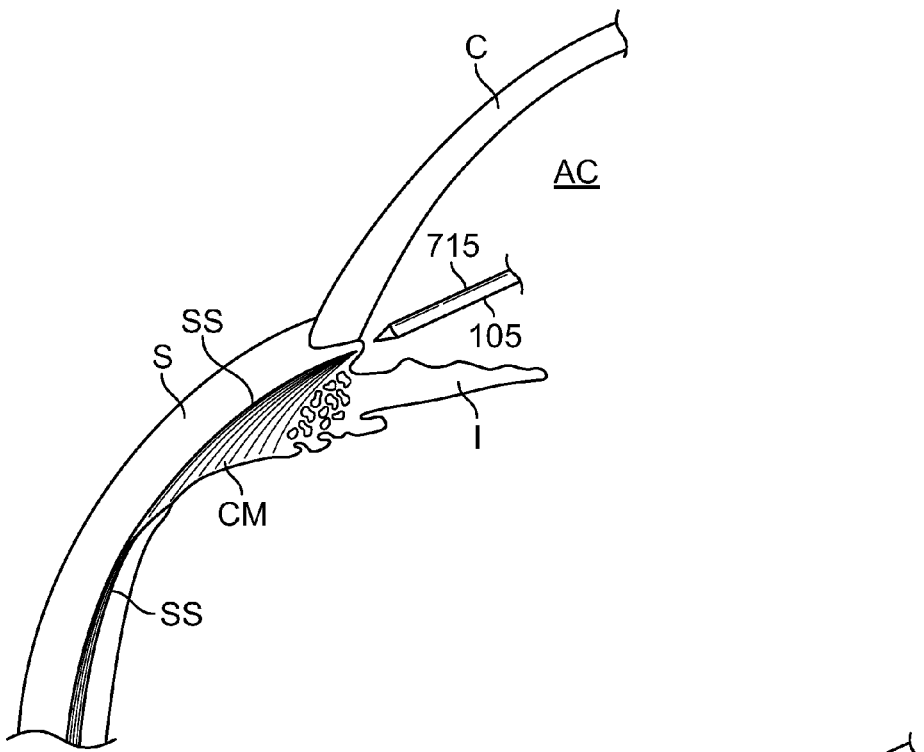
FIG. 12 shows an enlarged view of the anterior region of the eye with a portion of the delivery system positioned in the anterior chamber.

FIG. 12 shows an enlarged view of the anterior region of the eye. After insertion through the incision, the implant mounted on the delivery wire 715 is advanced through the cornea into the anterior chamber along a pathway that enables the implant to be delivered to a position such that the implant provides a flow passageway from the anterior chamber into the suprachoroidal space. The applier travels along a pathway that is toward the scleral spur such that the applier passes near the scleral spur on the way to the suprachoroidal space. The scleral spur is an anatomic landmark on the wall of the angle of the eye. The scleral spur is above the level of the iris but below the level of the trabecular meshwork. In some eyes, the scleral spur can be masked by the lower band of the pigmented trabecular meshwork and be directly behind it. In a preferred embodiment, the applier does not pass through the scleral spur during delivery. Rather, the applier abuts the scleral spur and then moves downward to dissect the tissue boundary between the sclera and the ciliary body, the dissection entry point starting just below (posterior) the scleral spur. The applier can penetrate the iris root or a region of the ciliary body or the iris root part of the ciliary body near its tissue border with the scleral spur. The combination of delivery wire properties and the angle of approach allows the procedure to be performed "blind" as the instrument tip follows the inner curve of the scleral wall to dissect the tissue and create a mini cyclo-dialysis channel to connect the anterior chamber to the suprachoroidal space. The surgeon can rotate or reposition the handle of the delivery device in order to obtain a proper approach trajectory for the distal tip of the applier, as described in further detail below. The delivery wire 715 can be pre-shaped, steerable, articulating, or shapeable in a manner that facilitates the applier approaching the suprachoroidal space along a proper angle or pathway.

As mentioned, the scleral spur is not necessarily penetrated during delivery. If penetration of the scleral spur is desired, penetration through the scleral spur can be accomplished in various manners. In one embodiment, a sharpened distal tip of the applier or the implant punctures, penetrates, dissects, pierces or otherwise passes through the scleral spur toward the suprachoroidal space. The crossing of the scleral spur or any other tissue can be aided such as by applying energy to the scleral spur or the tissue via the distal tip of the delivery wire 715. The means of applying energy can vary and can include mechanical energy, such as by creating a frictional force to generate heat at the scleral spur. Other types of energy can be used, such as RF laser, electrical, etc.

Figure 13:
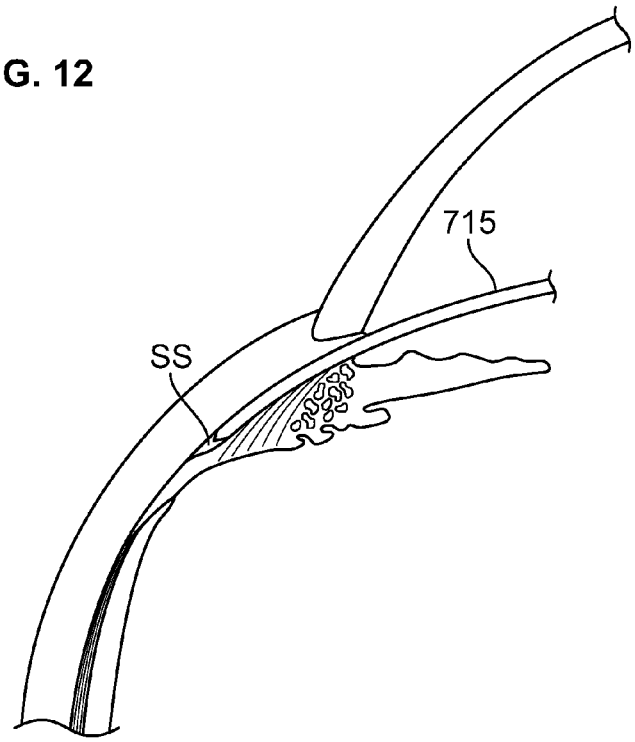
FIG. 13 shows the distal tip of a delivery system positioned within the suprachoroidal space.

FIG. 13 shows the distal tip of the delivery wire 715 positioned within the suprachoroidal space SS. For clarity of illustration, FIG. 13 does not show the implant 105 mounted on the applier, although the implant 105 is mounted on the applier during delivery. As the delivery wire 715 advances through tissue, the distal tip causes the sclera to peel away or otherwise separate from the ciliary body or the choroid. As mentioned above, a variety of parameters including the shape, material, material properties, diameter, flexibility, compliance, pre-curvature and tip shape of the delivery wire 715 make it more inclined to follow an implantation pathway that mirrors the natural pathway between tissue layers, for example between tissue layers the sclera and choroid, and the curvature of the eye. The delivery wire 715 is continuously advanced into the eye, until the distal tip is located at or near the suprachoroidal space such that a first portion of the implant 105 is positioned within the suprachoroidal space and a second portion is positioned within the anterior chamber. In one embodiment, at least 1 mm to 2 mm of the implant (along the length) remains in the anterior chamber. The implant 105 is then released from the delivery wire in the manner described above with reference to FIGS. 6A-6C or FIGS. 7A-7C.

Cyclodialysis Procedure

In another embodiment, a cyclodialysis procedure is performed using an alternate embodiment of the delivery system 905. In this embodiment, the delivery wire 715 is a needle with a sharpened distal tip such that the needle can puncture, dissect, or otherwise form a passageway into the suprachoroidal space from the anterior chamber. Either immediately before or after a cataract procedure (or during the procedure) on the eye, the distal tip of the needle is used to form a micro cyclodialysis dissection. This forms a vent between the anterior chamber and the suprachoroidal space that can serve to vent pressure from the anterior chamber into the suprachoroidal space. In an embodiment, the needle is heated to heat-set the eye tissue around it so that the micro-cyclodialysis has more of a tendency to remain open for a desired time period. The micro-cyclodialysis may remain open for a period of 3 hours to 24 hours. In an embodiment, the micro-cyclodialysis remains open for 8 hours or for an overnight period. A fast resorbing implant (i.e., resorbs within 8 hours) can be implanted into the passageway formed by the micro-cyclodialysis. The implant has a passageway that connects the anterior chamber and suprachoroidal space.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A system for treating an ocular disorder in a patient, comprising:
    an elongate member defining a flow pathway, at least one inflow port communicating with the flow pathway, and an outflow port communicating with the flow pathway, wherein the elongate member includes a first, proximal portion formed of a non-expandable, solid tube overlayed with a spring-loaded, braided, expandable material structure and a second, distal portion formed entirely of the spring-loaded, braided, expandable material structure, which is configured to form a first length and a first outer diameter when in tension and form a second length and a second outer diameter upon release of tension, wherein the first length is longer than the second length and the first outer diameter is smaller than the second outer diameter, the braided, expandable material structure including a distal end secured by a solid bullet-nose structure, wherein the elongate member is configured to be implanted through a self-sealing corneal incision and positioned in the eye such that the inflow port communicates with the anterior chamber and the outflow port communicates with the suprachoroidal space and wherein the distal portion has one or more openings that expand in size when the distal portion changes shape; and
    a delivery device having a delivery component that removably attaches to the elongate member, wherein the delivery component is configured to secure the second, distal portion of the elongate member in an unexpanded state during delivery of the elongate member into an eye, and wherein the delivery component secures to the elongate member via a press fit,
    wherein the delivery component is a wire that applies a distally-directed force against the solid bullet-nose structure of the distal portion of the elongate member while the elongate member is mounted on the wire.

2. A system as in claim 1, wherein at least a portion of the second distal portion is configured to be secured in an unexpanded state during delivery of the elongate member into an eye.

3. A system as in claim 2, wherein the delivery component is further comprised of a sheath to constrain at least a portion of the implant.

4. A system as in claim 2, wherein the delivery component is configured to plastically expand the implant to a second shape after delivery into an eye.

5. A system as in claim 2, wherein the delivery component is configured to deliver a fluid medium to plastically expand the second distal portion.

6. A system as in claim 2, wherein the delivery device is configured to impart an axial force on the implant to plastically expand the second distal portion.

7. A system as in claim 1, wherein the braided, expandable material structure is a mesh.

* * * * *